(12) United States Patent
Hammett

(10) Patent No.: US 6,332,534 B1
(45) Date of Patent: Dec. 25, 2001

(54) SYSTEM FOR SAFE DISPOSAL OF SHARP INSTRUMENTS

(75) Inventor: Roy Hammett, Tampa, FL (US)

(73) Assignee: Innovative Consumer Products, Inc., Tampa, FL (US)

( * ) Notice: Subject to any disclaimer, the term of this patent is extended or adjusted under 35 U.S.C. 154(b) by 0 days.

(21) Appl. No.: 09/458,662

(22) Filed: Dec. 10, 1999

(51) Int. Cl.[7] ................................................. B65D 83/10
(52) U.S. Cl. .................... 206/366; 206/524.4; 604/110
(58) Field of Search ................................. 206/363–366, 206/372, 373, 222, 219, 524.4, 814; 604/82, 192, 263, 110; 220/908, 608

(56) References Cited

U.S. PATENT DOCUMENTS

| | | | |
|---|---|---|---|
| 2,766,755 | * 10/1956 | Greene | 206/222 |
| 4,845,923 | * 7/1989 | Donovan | 206/366 |
| 4,919,264 | * 4/1990 | Shinall | 206/366 |
| 4,973,315 | * 11/1990 | Sincock | 206/365 |
| 5,038,929 | * 8/1991 | Kubofcik | 206/366 |
| 5,084,027 | * 1/1992 | Bernard | 604/263 |
| 5,211,285 | * 5/1993 | Haber et al. | 206/221 |
| 5,322,165 | * 6/1994 | Melker et al. | 206/366 |
| 5,334,400 | * 8/1994 | Purdham | 206/219 |
| 5,687,444 | * 11/1997 | Hakker | 220/608 |
| 6,123,193 | * 9/2000 | Vojtasek et al. | 206/366 |

* cited by examiner

*Primary Examiner*—Luan K. Bui

(57) ABSTRACT

In accordance with the invention, a container is provided for receiving at least the sharp portion of at least one medical instrument. The container has a wall on one end penetrable by the sharp instrument, and is separated into two fluid-tight compartments by a frangible membrane. One of the compartments contains a hardenable substance, such as epoxy, resin or other material, and the second compartment is configured to have a small internal free volume and contains an activator to react with the hardenable material to cause it to quickly harden when the two are admixed. The hardened material bonds to and encapsulates the sharp portion of the instrument, rendering it incapable of further use.

15 Claims, 5 Drawing Sheets

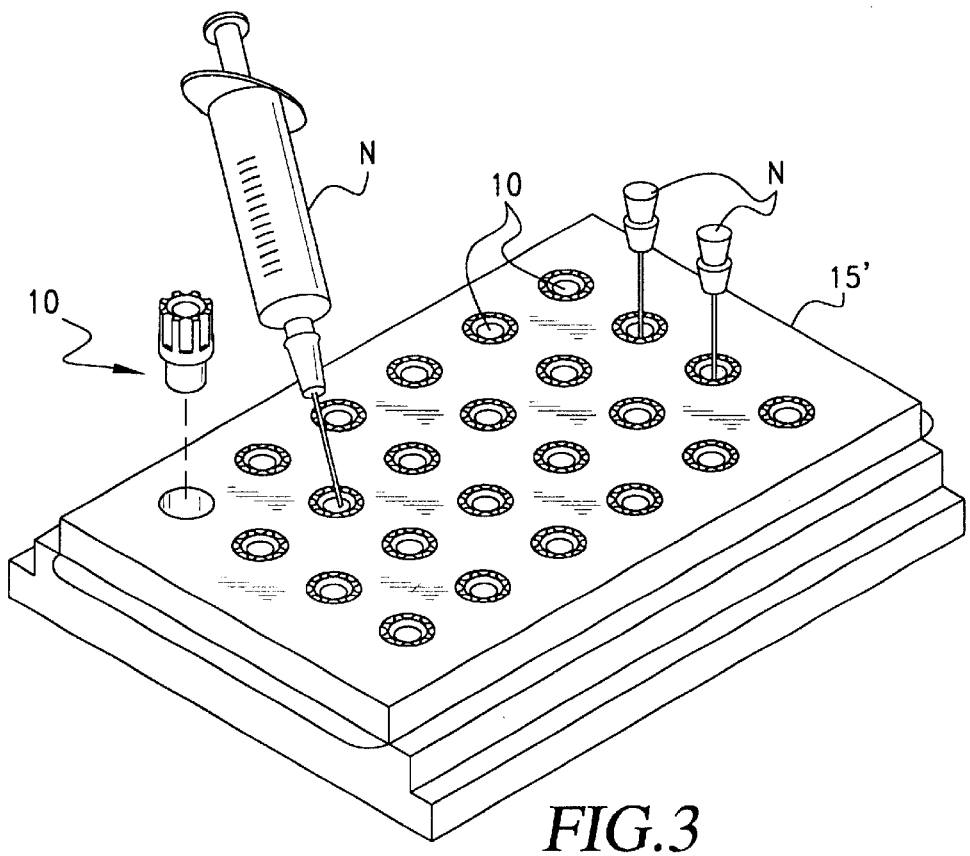
FIG.3
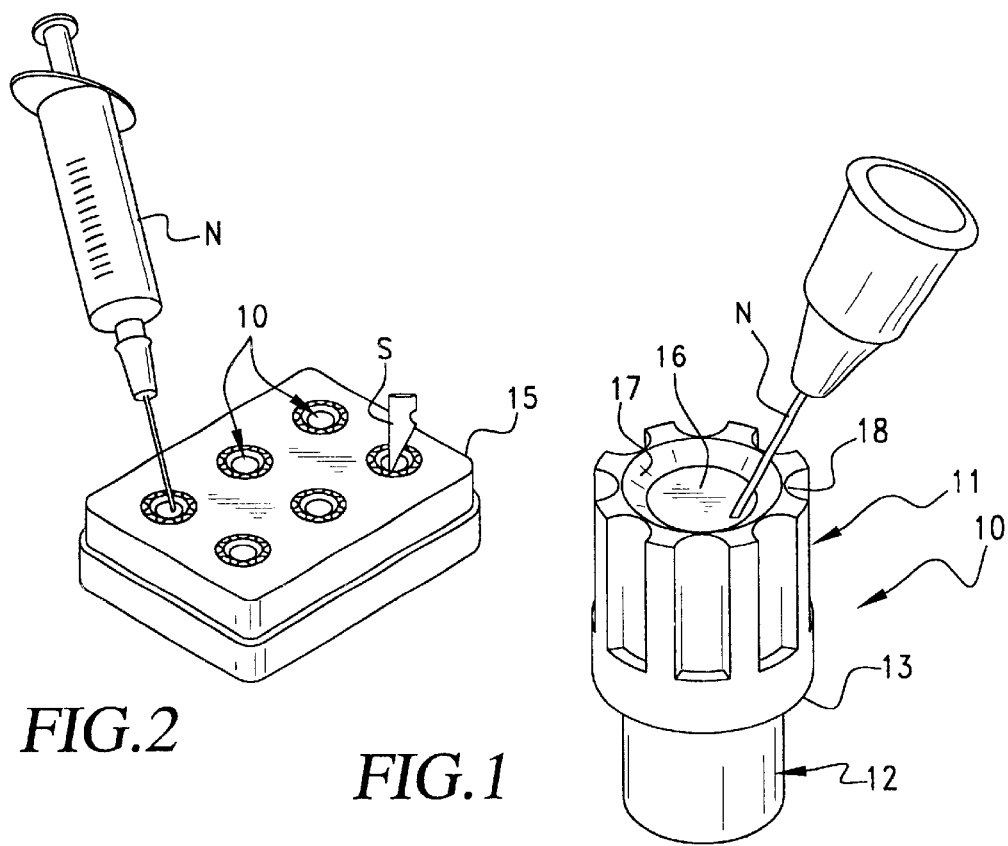
FIG.2
FIG.1

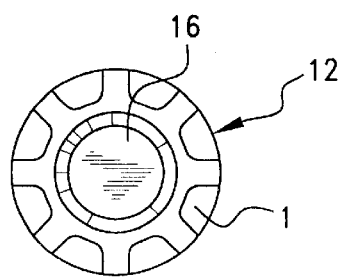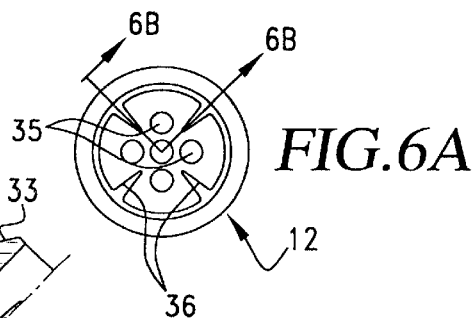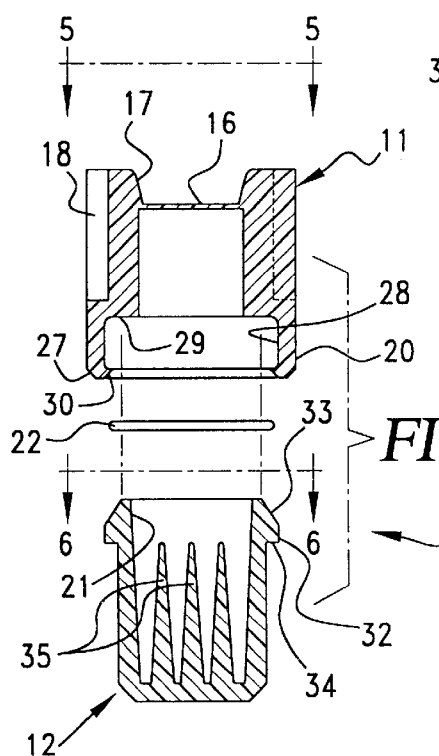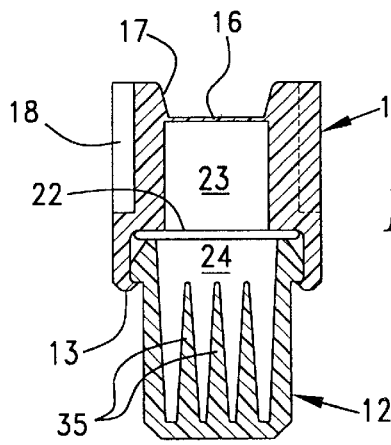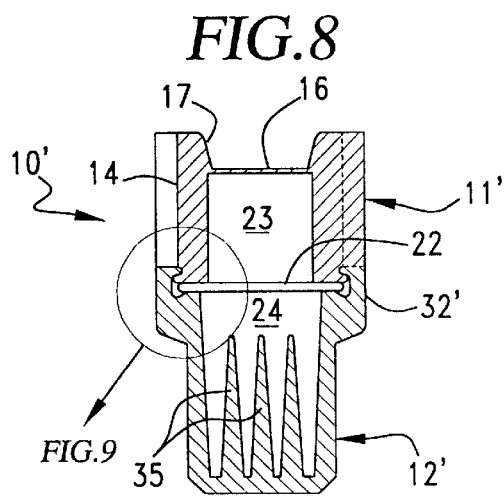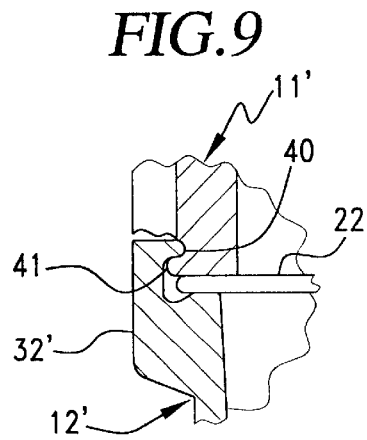

SYSTEM FOR SAFE DISPOSAL OF SHARP INSTRUMENTS

BACKGROUND OF THE INVENTION

1. Field of the Invention

This invention relates to systems for the safe disposal of medical instruments having sharp edges or points that may have been contaminated by infectious diseases or other harmful organisms. More particularly, the invention relates to a device for the rapid and safe disposal at the point of use of at least the sharp portion of used medical instruments such as, e.g., hypodermic needles, scalpel blades, suturing needles and lancets.

The present invention is an improvement over the system disclosed in U.S. Pat. No. 5,322,165, licensed to applicant herein.

2. Prior Art

The safe disposal of medical instruments contaminated during a medical procedure with tissue and body fluids is a major health concern. Infectious diseases such as the AIDS virus and hepatitis, for example, can be transmitted through contact with contaminated instruments. Hypodermic needles, trocars and other instruments having sharp edges or points are particularly dangerous to personnel handling them. Disposing of the used medical instruments within the operating rooms, patient rooms, laboratories and other facilities is a task that exposes the doctors, nurses and other personnel to the risk of being inadvertently stuck or pricked by the contaminated sharp instruments. Injuries frequently have occurred, for instance, while attempting to cap used hypodermic needles in preparation for their transport and disposal through incineration or other means.

Current procedures require the collection and removal of the dangerous "sharps" to another site for decontamination, encapsulation or other protective measures. This means that the unprotected medical instruments could be retrieved and reused by unauthorized persons between the time the instruments are used in a medical procedure and the time they are destroyed or rendered incapable of further use.

Numerous devices and systems have been developed in the prior art in an effort to solve the problem of safe disposal of contaminated medical instruments.

Prior U.S. Pat. Nos. 4,816,307 and 4,900,500 to Honeycutt, and U.S. Pat. No. 4,845,923 to Donovan, disclose methods for encasing "sharps" in containers having resins which harden and encapsulate the instruments. The processes disclosed in these patents are slow reacting, do not provide a capsule that is resistant to crushing, and in some cases require handling of chemicals by the staff at the point of use.

U.S. Pat. No. 5,322,165 to Melker, et al., discloses an instrument encasement system in which a container is divided into two compartments by a frangible membrane, one compartment containing a hardenable resin and the other compartment containing a particulate filler and an activator. Upon insertion of a medical instrument through a penetrable top and through the frangible membrane, the contents of the compartments mix, creating a reaction that quickly hardens the resin and particulate material mixture and encases the sharp portions of the medical instrument. The system described in this patent does provide a quick reaction time for hardening of the resin and also provides a capsule or container for holding the sharps. However, a relatively large volume of resin is required, in spite of the use of the filler, and manufacturing difficulties may be encountered, particularly with reference to the placement of the frangible disc and the penetrable end wall.

Accordingly, there is need for a system for the rapid and safe disposal at the point of use of used medical instruments, wherein the system is simple and economical in construction.

SUMMARY OF THE INVENTION

The present invention provides a device and system for the rapid and safe disposal at the point of use of used medical instruments, wherein the system is simple and economical in construction and is easy to use.

In accordance with the invention, a container is provided for receiving at least the sharp portion of at least one medical instrument. The container has a wall on one end penetrable by the sharp instrument, and is separated into two fluid-tight compartments by a frangible membrane. One of the compartments contains a hardenable substance, such as epoxy, resin or other material, and the second compartment is configured to have a small internal free volume and contains an activator to react with the resin, epoxy or other hardenable material to cause it to quickly harden when the two are admixed. The hardened material bonds to and encapsulates the sharp portion of the instrument, rendering it incapable of further use.

The small internal volume of the second compartment enables less hardenable material to be used, and results in quicker mixing of the material and the activator and consequent quicker hardening of the material when the frangible membrane is broken. Moreover, the structure forms a large surface area for bonding with the hardenable substance, thereby securely bonding the instrument to the container.

For ease of manufacture, the container comprises two parts which may be joined together with the frangible membrane between them to form the two compartments. Prior to assembly, the hardenable substance and the activator may be suitably placed in the respective compartments.

In a preferred embodiment, the hardenable substance may comprise a cyanoacrylate resin (CA), and the activator may comprise sodium bicarbonate or sodium hydroxide. Other suitable multi-part adhesive compositions may be used.

The hardenable substance preferably comprises a liquid of low viscosity, i.e., similar to the viscosity of water, and the activator may be liquid or particulate and placed loose in its compartment, or coated onto the internal surface of the compartment.

In one embodiment of the invention, the compartment comprises a glass ampoule divided into two compartments by a frangible membrane, and held within a housing having a top with a wall penetrable by the sharp instrument.

In a preferred construction, the container has a width of about one-half inch and a length or depth of about one inch. It should be understood, however, that the container could have other sizes, as desired. Moreover, the container can be made of any suitable material, although plastic is preferred. The frangible membrane preferably comprises a thin glass disc, such as that available from Erie Scientific of Portsmouth, N.H., for use as a microscope cover glass. These discs come in a range of thicknesses, but a thickness of about 0.004 inch is preferred. If desired, the disc can be scored or etched to make it more frangible.

For ease of handling and disposal, a plurality of the containers may be held in a suitable structure. One suitable arrangement comprises a tray-like housing having a plurality of recesses or openings therein for receiving the containers.

The containers may be lifted from the tray and disposed of one-by-one, or left in the tray until all of the containers have been used, and then disposed of as a group along with the tray.

BRIEF DESCRIPTION OF THE DRAWINGS

The foregoing as well as other objects and advantages of the invention will become apparent from the following detailed description when considered in conjunction with the accompanying drawings, wherein like reference characters designate like parts throughout the several views, and wherein:

FIG. 1 is a top perspective view of an encapsulation device according to the invention, showing a hypodermic syringe needle encapsulated therein;

FIG. 2 is a top perspective view of a system in accordance with the invention, wherein a plurality of containers or encapsulation devices are held in a tray-like housing, and showing a variety of medical instruments held by the containers;

FIG. 3 is a top perspective view similar to FIG. 2, but showing a larger tray for holding a greater quantity of containers according to the invention;

FIG. 4 is an exploded view in longitudinal section of a container according to the invention;

FIG. 5 is an end view of the top portion of the container of FIG. 4, looking in the direction of the arrow "5" in FIG. 4;

FIG. 6A is an end view of the bottom portion of the container of FIG. 4, looking in the direction of the arrow "6" in FIG. 4;

FIG. 6B is a fragmentary sectional view taken along line 6B—6B in FIG. 6A;

FIG. 7 is a longitudinal sectional view of the assembled container according to a first form of the invention;

FIG. 8 is a longitudinal sectional view of the assembled container according to a second form of the invention;

FIG. 9 is an enlarged fragmentary sectional view of the area circled at "9" in FIG. 8;

FIGS. 10–14 are longitudinal sectional views depicting the sequence of steps in filling and assembling the encapsulation device of the invention, wherein FIG. 10 shows an activator placed in the bottom portion of the container, FIG. 11 shows the top portion of the container inverted or turned upside down and a hardenable liquid substance placed therein, FIG. 12 shows a band of adhesive placed on an annular shoulder in the bottom portion, FIG. 13 shows a glass disc seated on the shoulder and band of adhesive, and FIG. 14 shows the top portion of the container turned right side up and assembled with the lower portion;

FIG. 16 is an exploded longitudinal sectional view of a further modified form of the invention, wherein the components of the hardenable substance are held in separate compartments in a glass vial or ampoule that is, in turn, held in a housing;

DETAILED DESCRIPTION OF THE PREFERRED EMBODIMENTS

Figure 20:
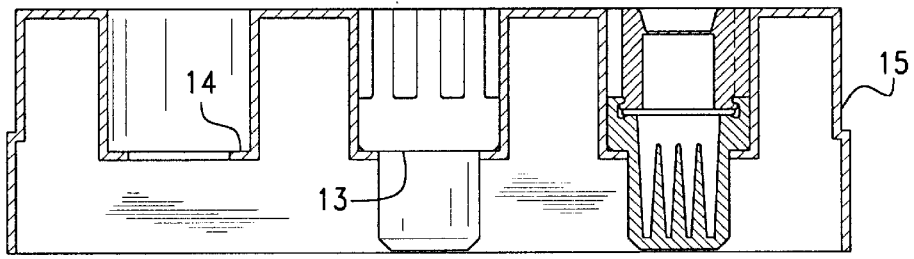
FIG. 20 is a transverse sectional view taken along line 20—20 in FIG. 19.
Figure 21:
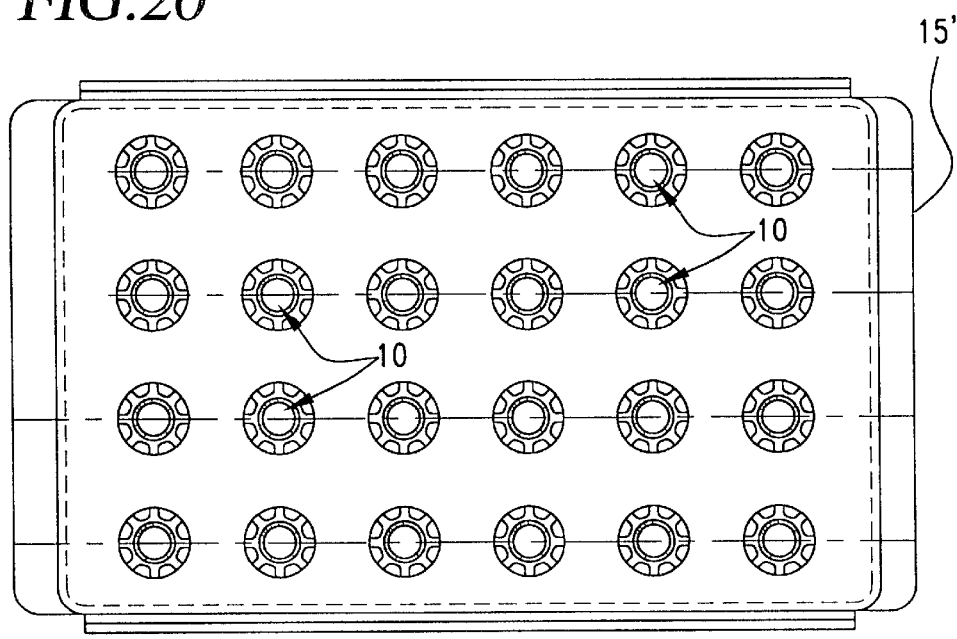
FIG. 21 is a top plan view of a larger tray-like housing holding a plurality of containers according to the invention.

An encapsulation device according to the invention is indicated generally at 10 in the drawings. In a preferred construction, the encapsulation device comprises an upper body portion 11 and a diametrically reduced lower body portion 12 defining an annular, downwardly facing shoulder 13 that may support the device on a complementary ledge 14 in tray-like housing 15 (see FIG. 20). However, the encapsulation device can be used independently of other structure, and it is not necessary that it be supported in a tray 15.

The upper body portion has a penetrable recessed end wall 16 surrounded by a tapered wall 17 that facilitates guiding of a needle N or other sharp instrument S, whereby a doctor, nurse or other person can quickly and easily insert the needle or other sharp instrument through the wall and into the encapsulation device. The upper body portion also has a longitudinally ribbed outer surface 18.

As seen best in FIGS. 4–15, the upper and lower body portions are both generally cup-shaped, having open first ends 20 and 21, respectively, disposed in confronting, contiguous relationship to one another in the assembled device, defining an enclosed chamber. A frangible membrane 22 is secured between the open ends, separating the enclosed chamber into two separate fluid-tight compartments 23 and 24 (see FIG. 7).

A first of the compartments 23 contains a suitable hardenable substance or adhesive 25, and the second compartment 24 contains a suitable accelerator or hardener 26 to react with the adhesive when the frangible membrane 22 is broken and the adhesive and accelerator are mixed together to cause the adhesive to harden in a short period of time, e.g., about two or three seconds.

With reference particularly to FIGS. 4, 6A and 6B, the first end of the upper body portion 11 has a beveled surface 27, is internally diametrically enlarged at 28, defining an internal annular downwardly facing shoulder 29, and has a radially inwardly directed annular rib or flange 30 in the open end 20.

The lower body portion 12 has an external radially enlarged annular flange 32 on its open first end 21, with an outer beveled upper end portion 33 and a downwardly facing shoulder 34. A plurality of closely spaced spikes or prongs 35 and ribs 36 project upwardly in the body portion 12, extending over most of its length and occupying a substantial part of the volume of the compartment 24.

As shown in FIG. 7, the upper and lower body portions are secured together by snapping the flange 32 on the first end of the lower body portion behind the rib 30 on the first end of the upper body portion, with the frangible membrane 22 clamped between the first end of the lower body portion and the shoulder 29 in the upper body portion. If desired, an adhesive may be used to further secure the upper and lower body portions together.

A variation of the above-described structure is indicated generally at 10' in FIGS. 8 and 9. In this form of the invention, the upper and lower body portions 11' and 12' are constructed substantially identically to the form previously described, except that the relationship of the interengaged flanges and ribs is reversed, i.e., the flange 32' on the upper end of the lower body portion is arranged to engage over or on the outside of the lower end of the upper body portion, rather than inside it as previously described. A radially inwardly directed annular bead 40 on the inside upper surface of the flange 32' is adapted to snap behind a complementary radially outwardly directed bead 41 on the lower end of the upper body portion to secure the upper and lower body portions together.

Figure 10:
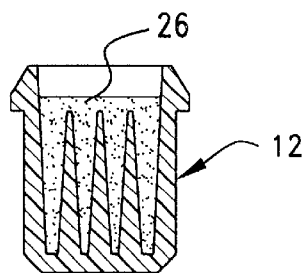

A process of filling and assembling the encapsulation devices 10 and/or 10' is depicted in FIGS. 10–14. As shown in FIG. 10, the accelerator 26 is placed in the compartment in the lower body portion 12 (or 12'). Although the accelerator is depicted in this figure as comprising a quantity of material placed in the compartment, it is to be understood that as an alternative the interior surface of the lower body portion could be suitably treated or coated with the accelerator material.

Figure 11:
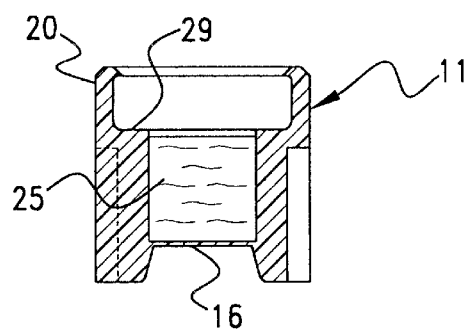

In FIG. 11, the upper body portion 11 is shown inverted so that its open end 20 is upwardly disposed, and the hardenable substance 25 is placed in the compartment 23 to approximately the level of the shoulder 29, or slightly below the shoulder.

Figure 12:
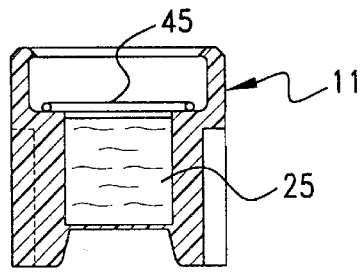
Figure 13:
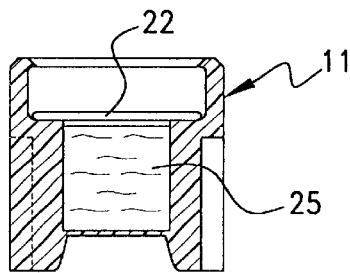

A bead of adhesive 45 is next placed on the shoulder 29, as shown in FIG. 12, and the frangible membrane 22 is pressed onto the bead of adhesive to secure and seal the membrane to the lower body portion, enclosing and sealing the hardenable substance 25 in the compartment 23, as shown in FIG. 13.

Figure 14:
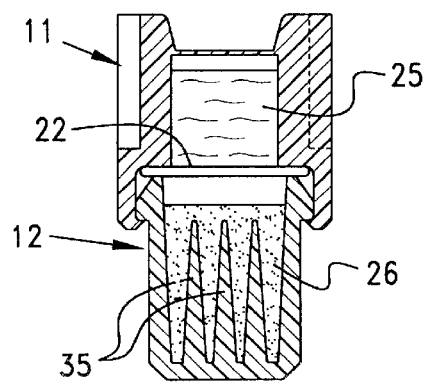
Figure 15:
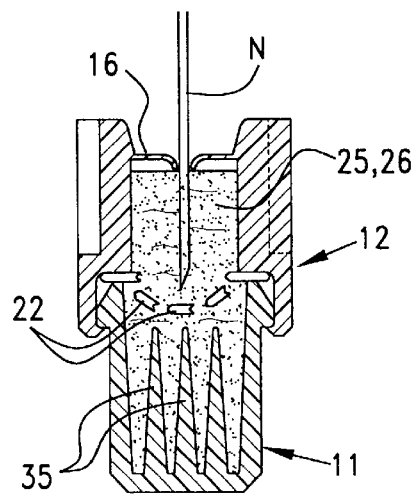
FIG. 15 shows a needle penetrating the top wail and breaking the frangible membrane to enable the components in the two compartments to admix and harden to encapsulate the needle and render it useless.

The two body portions are then snapped together, with or without the use of adhesive, to form the completed encapsulation device 10 as shown in FIG. 14.

In use, a needle N or other sharp instrument is inserted through the penetrable wall 16 and into the interior of the encapsulation device to contact and break the frangible membrane 22, permitting the accelerator 26 to mix with the hardenable substance or adhesive 25, causing a reaction that hardens the hardenable substance within two or three seconds. The adhesive bonds with the needle or other sharp instrument and with the interior of the encapsulation device, permanently affixing the needle or other instrument to the encapsulation device and rendering the needle or other instrument incapable of further use. In this regard, it should be noted that the adhesive also flows into the interior of hollow instruments, such as needle N, when the instrument is inserted into the encapsulation device, further ensuring that the instrument cannot be reused.

The spikes or prongs 35 serve to reduce the volume of the chamber and thus the quantity of hardenable substance that must be used, and also serve to form a larger bonding surface for the adhesive and thus an enhanced mechanical lock between the hardened adhesive, the needle or other instrument, and the encapsulation device.

The frangible membrane 22 preferably comprises a glass disc having a thickness of about 0.004 inch and available from Erie Scientific of Portsmouth, N.H., as microscope cover glass. If desired, this disc may be suitably etched or scored or otherwise treated to increase its frangibility. It is desired that this disc fracture into many small pieces when it is contacted by the instrument inserted into the encapsulation device, so that the liquid adhesive and the accelerator can quickly intermix with one another. Further, it may be necessary to treat the surface of the frangible glass membrane with sulfuric acid to prevent a skin from forming on the surface of the glass in contact with the adhesive.

Although any suitable materials may be used in the construction of the invention, in a preferred embodiment the upper body portion 11 may be made of a low density polyethylene (LDPE), and the lower body portion 12 may be made of a general purpose polystyrene for better bonding with the adhesive.

For greater ease and efficiency of use, the encapsulation devices may be placed in a tray 15 or 15' of appropriate size to hold a desired quantity of the encapsulation devices. The trays may be made of any suitable material, including general purpose polyethylene (GPPE) or high density polyethylene (HDPE). Used medical sharps are inserted into respective encapsulation devices, which may simply be left in the tray for later disposal of the entire tray, or the individual encapsulation devices containing used sharps may be withdrawn from the tray for disposal.

Figure 17:
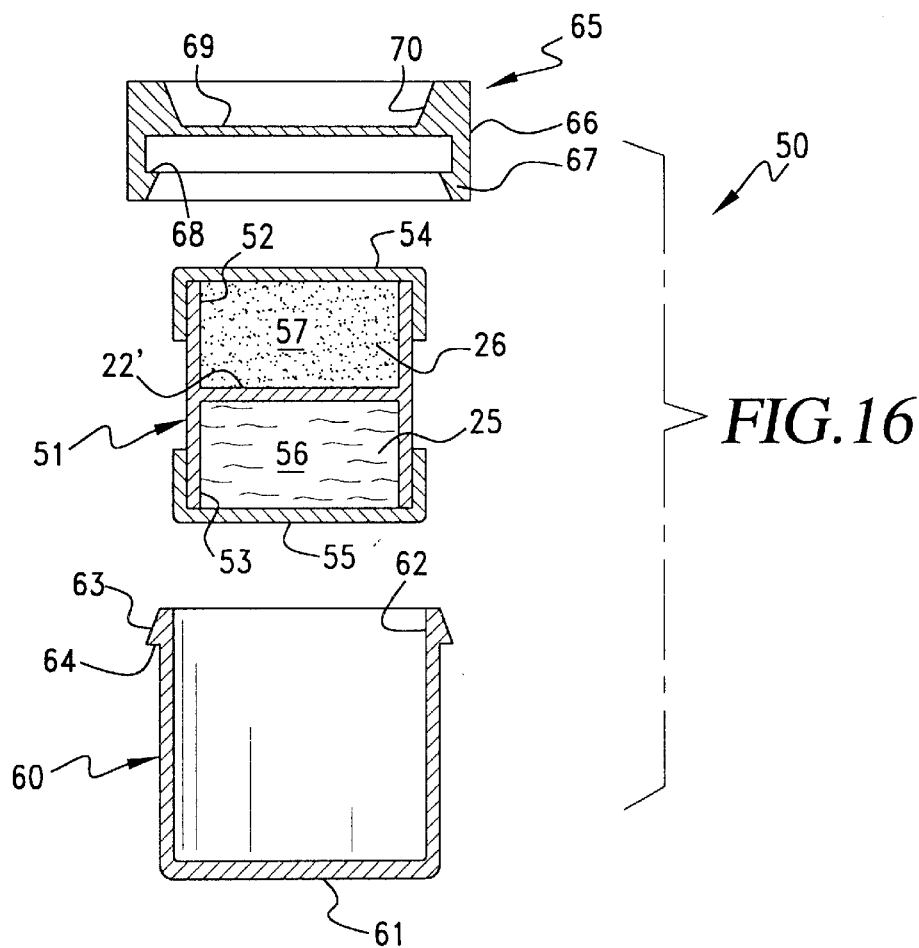
FIG. 17 is longitudinal sectional view of the device of FIG. 16, shown assembled.
Figure 18:
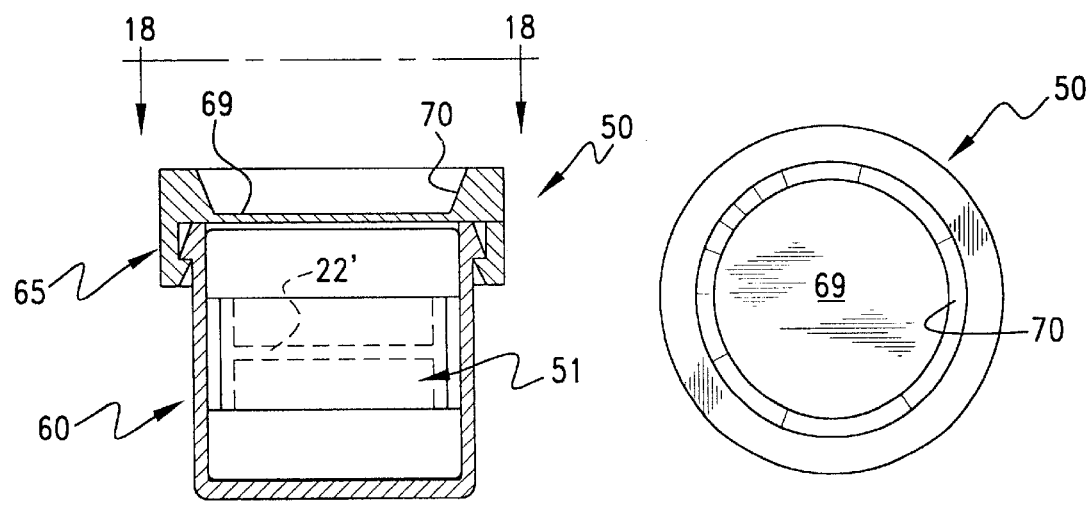
FIG. 18 is an end view of the device of FIG. 17, taken in the direction of the arrow "18" in FIG. 17.
Figure 19:
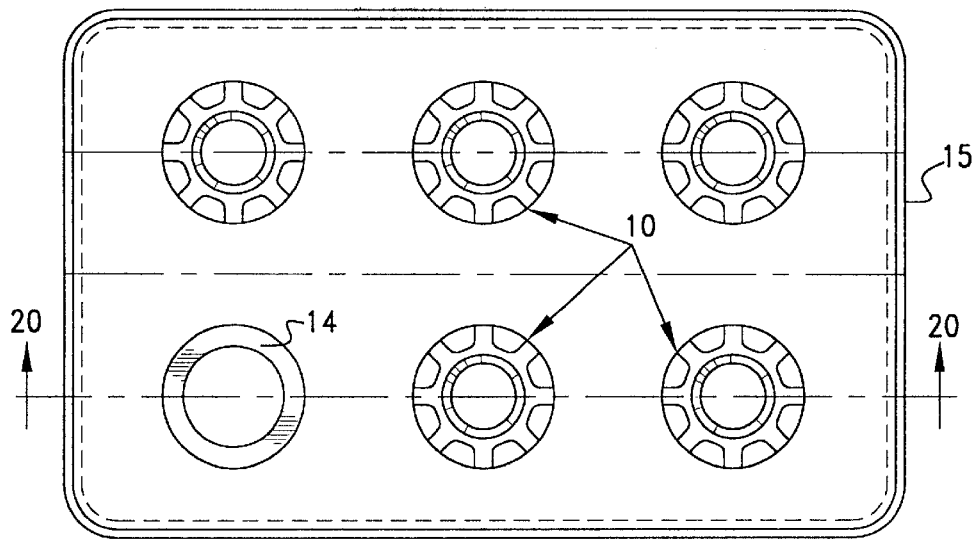
FIG. 19 is a top plan view of a tray-like housing holding a plurality of containers according to the invention.

A further embodiment of the encapsulation device is indicated generally at 50 in FIGS. 16–18. In this form of the invention, the encapsulation device comprises a glass ampoule 51 having open opposite ends 52 and 53 closed by covers 54 and 55, respectively. A frangible membrane 22' extends across the interior of the ampoule, dividing it into a first compartment 56 and a second compartment 57, containing a hardenable substance 25 and an accelerator 26, respectively, as in the previous forms of the invention. While the two compartments are shown in these figures as of approximately the same size, it should be understood that the compartments could be different sizes, as desired. For example, the compartment 57 containing the accelerator 26 could be smaller than the compartment 56.

The ampoule 51 is confined within a housing 60 of generally cup-shaped configuration, having a closed bottom 61 and an open top 62 surrounded by an annular flange 63 that defines an axially downwardly facing shoulder 64.

A cap 65 closes the open end of the housing 60 and has a relatively short depending wall or skirt 66 with an annular flange 67 on its lower inside surface, defining an annular upwardly facing shoulder 68 that engages behind the shoulder 64 to secure the cap to the housing 60. A thin, penetrable wall 69 extends across the cap in recessed relationship to its upper end, and is surrounded by a tapered surface 70.

This modified encapsulation device is used in essentially the same manner as that previously described, i.e., a needle or other sharp instrument is inserted through the penetrable wall 69 and through one of the covers 54 or 55 and the frangible membrane 22' to fracture the membrane and cause the hardenable substance and accelerator to mix, capturing the needle or other sharp instrument and rendering it incapable of further use. The covers 54 and 55 may be made of glass or other suitable material, and may be frictionally or otherwise secured in place.

The invention provides a simple, economical and effective means for the quick and safe disposal at the point of use of contaminated sharp medical instruments.

While particular embodiments of the invention have been illustrated and described in detail herein, it should be understood that various changes and modifications may be made to the invention without departing from the spirit and intent of the invention as defined by the scope of the appended claims.

What is claimed is:

1. A system for the safe disposal of sharp instruments, comprising:
   a container having an upper body portion and a lower body portion, each with first and second ends, secured together at their respective first ends to define a hollow interior;
   a frangible membrane extending across the interior of the container, between the secured-together first ends of the upper and lower body portions, separating the interior into a first fluid-tight compartment and a second fluid-tight compartment, said second fluid-tight compartment being in said lower body portion;

a hardenable liquid substance in the first compartment, and an accelerator in the second compartment;

at least one protuberance extending upwardly in said second compartment, occupying a part of the volume of said second compartment, and defining a large surface area, whereby less hardenable substance is required in order to effectively encapsulate said sharp instrument and an enhanced mechanical bond is achieved between the hardenable substance, the sharp instrument, and the container; and a penetrable wall extending across the second end of the upper body portion, so that a sharp instrument may be penetrated through the wall into the container and into contact with the frangible membrane to fracture the membrane and permit rapid admixing of the hardenable substance and the accelerator to cause a reaction to harden the hardenable substance and capture the instrument, rendering the instrument incapable of further use.

2. A system as claimed in claim 1, wherein:

said upper and lower body portions are secured together by snap-engaging means on their respective first ends.

3. A system as claimed in claim 2, wherein:

said frangible membrane is glass and is clamped between said first ends of said upper and lower body portions.

4. A system as claimed in claim 3, wherein:

said frangible membrane is adhesively secured and sealed to said first end of the upper body portion.

5. A system as claimed in claim 4, wherein:

said hardenable substance comprises a cyanoacrylate ester; and said accelerator comprises a strong base.

6. A system as claimed in claim 5, wherein:

said accelerator comprises sodium bicarbonate.

7. A system as claimed in claim 5, wherein:

said accelerator comprises sodium hydroxide.

8. A system as claimed in claim 7, wherein:

said lower body portion is made of general purpose polystyrene.

9. A system for the safe disposal of sharp instruments, comprising:

a container having an upper body portion and a lower body portion defining a hollow interior;

frangible means separating the interior of the container into a first fluid-tight compartment and a second fluid-tight compartment;

a hardenable liquid substance in one of the compartments, and an accelerator in the other compartment;

a penetrable wall extending across an end of the upper body portion, so that a sharp instrument may be penetrated through the wall into the container and into contact with the frangible means to fracture the frangible means and permit rapid admixing of the hardenable substance and the accelerator to cause a reaction to harden the hardenable substance and capture the instrument, rendering the instrument incapable of further use; and means protruding into said other compartment, occupying a part of the volume of said other compartment, and defining a large surface area, whereby less hardenable substance is required in order to effectively encapsulate said sharp instrument and an enhanced mechanical bond is achieved between the hardenable substance, the sharp instrument and the container.

10. A system as claimed in claim 9, wherein:

said means protruding into said other compartment comprises a plurality of closely spaced spikes extending upwardly into the interior of said other compartment.

11. A container having a hollow interior for receiving and encapsulating at least the sharp portion of at least one sharp instrument, comprising:

a wall on one end of the container penetrable by the sharp instrument;

a frangible membrane separating the interior of the container into two fluid-tight compartments, one of the compartments containing a hardenable substance, and the second compartment containing an activator to react with the hardenable substance to cause it to quickly harden when the two are admixed; and said second compartment having an irregular internal surface configured to define a small internal volume, whereby less hardenable substance is required in order to effectively capture the sharp instrument and a greater surface area is provided for bonding with the hardenable substance.

12. A system for the safe disposal of sharp instruments, comprising:

a container having a hollow interior;

frangible means separating the interior of the container into a first fluid-tight compartment and a second fluid-tight compartment, said frangible means comprising a glass ampoule having a hollow interior and opposite closed ends, and a frangible membrane extending across the hollow interior of the ampoule, dividing it into said first and second compartments;

a hardenable liquid substance in one of the compartments, and an accelerator in the other compartment; and a penetrable wall extending across one end of the container, so that a sharp instrument may be penetrated through the wall into the container and into contact with the frangible means to fracture the frangible means and permit rapid admixing of the hardenable substance and the accelerator to cause a reaction to harden the hardenable substance and capture the instrument, rendering the instrument incapable of further use.

13. A system for the safe disposal of sharp instruments, comprising:

a container having an upper body portion and a lower body portion, each with first and second ends, secured together at their respective first ends to define a hollow interior;

said lower body portion being diametrically smaller than the upper body portion, defining an annular shoulder between the body portions, said shoulder comprising means on an outer surface of the container for supporting the container in a holder for holding a plurality of the containers;

a frangible membrane extending across the interior of the container, between the secured-together first ends of the upper and lower body portions, separating the interior into a first fluid-tight compartment and a second fluid-tight compartment;

a hardenable liquid substance in one of the compartments, and an accelerator in the other compartment; and a penetrable wall extending across the second end of the upper body portion, so that a sharp instrument may be penetrated through the wall into the container and into contact with the frangible membrane to fracture the membrane and permit rapid admixing of the hardenable substance and the accelerator to cause a reaction to harden the hardenable substance and capture the instrument, rendering the instrument incapable of further use.

14. A system for the safe disposal of sharp instruments, comprising:

a container having an upper body portion and a lower body portion, each with first and second ends, secured together at their respective first ends to define a hollow interior;

a frangible membrane extending across the interior of the container, between the secured-together first ends of the upper and lower body portions, separating the interior into a first fluid-tight compartment and a second fluid-tight compartment, said second fluid-tight compartment being in said lower body portion;

a hardenable liquid substance in the first compartment, and an accelerator in the second compartment;

a penetrable wall extending across the second end of the upper body portion, so that a sharp instrument may be penetrated through the wall into the container and into contact with the frangible membrane to fracture the membrane and permit rapid admixing of the hardenable substance and the accelerator to cause a reaction to harden the hardenable substance and capture the instrument, rendering the instrument incapable of further use; and at least one protuberance extending upwardly into said second compartment, occupying a part of the volume of said second compartment, and defining a large surface area, whereby less hardenable substance is required in order to effectively encapsulate said sharp instrument and an enhanced mechanical bond is achieved between the hardenable substance, the sharp instrument and the container.

15. A system for the safe disposal of sharp instruments, comprising:

a container having an upper body portion and a lower body portion, each with first and second ends, secured together at their respective first ends to define a hollow interior;

said lower body portion being diametrically smaller than the upper body portion, defining an annular shoulder on an outer surface thereof between the body portions that comprises a means for supporting the container in a holder for holding a plurality of the containers;

a frangible membrane extending across the interior of the container, between the secured-together first ends of the upper and lower body portions, separating the interior into a first fluid-tight compartment and a second fluid-tight compartment;

a hardenable liquid substance in one of the compartments, and an accelerator in the other compartment; and a penetrable wall extending across the second end of the upper body portion, so that a sharp instrument may be penetrated through the wall into the container and into contact with the frangible membrane to fracture the membrane and permit rapid admixing of the hardenable substance and the accelerator to cause a reaction to harden the hardenable substance and capture the instrument, rendering the instrument incapable of further use.

\* \* \* \* \*